United States Patent
Pedrazzini

(10) Patent No.: US 8,220,137 B2
(45) Date of Patent: Jul. 17, 2012

(54) APPARATUS FOR REMOVING CAPS FROM TUBULAR CONTAINERS

(75) Inventor: Gianandrea Pedrazzini, Paradiso (CH)

(73) Assignee: INPECO IP Ltd., Valletta (MT)

( * ) Notice: Subject to any disclaimer, the term of this patent is extended or adjusted under 35 U.S.C. 154(b) by 495 days.

(21) Appl. No.: 12/517,425

(22) PCT Filed: Dec. 4, 2006

(86) PCT No.: PCT/EP2006/069251
§ 371 (c)(1),
(2), (4) Date: Jul. 27, 2009

(87) PCT Pub. No.: WO2008/067844
PCT Pub. Date: Jun. 12, 2008

(65) Prior Publication Data
US 2010/0043211 A1    Feb. 25, 2010

(51) Int. Cl.
*B23P 19/00* (2006.01)
*B66C 1/42* (2006.01)
(52) U.S. Cl. .............. 29/709; 29/714; 29/244; 29/252; 29/283; 29/426.1; 294/86.4
(58) Field of Classification Search .............. 29/426.1, 29/426.5, 773, 709, 714, 243, 244, 252, 256, 29/261, 262, 283, 284; 294/86.4
See application file for complete search history.

(56) References Cited

U.S. PATENT DOCUMENTS

| | | | |
|---|---|---|---|
| 4,522,089 A | 6/1985 | Alvi | |
| 6,651,305 B2 * | 11/2003 | Fassbind et al. | 29/426.1 |
| 6,951,051 B2 * | 10/2005 | Wynn, Jr. | 29/426.5 |
| 2001/0013169 A1 | 8/2001 | Fassbind et al. | |

FOREIGN PATENT DOCUMENTS

| | | |
|---|---|---|
| EP | 0 972 744 A2 | 1/2000 |
| WO | WO-03/034038 A2 | 4/2003 |

\* cited by examiner

*Primary Examiner* — Jermie Cozart
(74) *Attorney, Agent, or Firm* — Birch, Stewart, Kolasch & Birch, LLP

(57) ABSTRACT

An apparatus for removing caps from tubular containers, including a fixed frame provided with a grasping unit for holding a container in a fixed vertical position and a head assembly which is movable above containers of variable height along the vertical axis thereof. The head assembly has a cap receiving cavity with an upper abutment surface for matching the upper surface of the cap of containers of variable size and is provided with a plurality of movable sharpened elements for catching the cap of the container when received in said cavity. There are provided a first driving unit for moving the sharpened elements towards the cap of the container to catch it and a second driving unit for moving the sharpened elements in at least one further direction to remove the cap from the container.

10 Claims, 15 Drawing Sheets

APPARATUS FOR REMOVING CAPS FROM TUBULAR CONTAINERS

BACKGROUND OF THE INVENTION

1. Field of the Invention

The present invention concerns a decapper system, that is an apparatus for removing caps from tubular specimen containers.

As used herein, the term "container" means an article that contains a biological specimen and has a cap-closed tubular opening for access of the contents, e.g., a test tube.

2. Description of the Related Art

In automated clinical chemistry laboratories, in order to access the biological specimen in the container, it is necessary to remove the cap from the container.

There are known decapper machines for pressure cap only and decapper machines for screw cap only.

In the decapper machines it is important not only to remove the pressure or screw cap without damaging it but also to be able to operate with containers of different size.

In addition, there is the problem that the container is to be removed from its carrier for the cap removal operation and then repositioned into the carrier. This may cause the potential risk that the container is repositioned into a different carrier thereby jeopardizing the specimen identification process in those cases in which the specimen identification is made through the container carrier identification.

BRIEF SUMMARY OF THE INVENTION

Object of the present invention is now to provide a decapper apparatus which allows safe removal of screw caps and pressure caps.

Another object is to provide a decapper apparatus which can be self-adapting to containers of different sizes.

A further object is to provide a decapper apparatus which is able to remove the cap without removing the container from its carrier.

In view of the above objects the apparatus according to the present invention for removing caps from tubular specimen containers is characterized by comprising a fixed frame provided with grasping means for holding a container in a fixed vertical position and a head assembly which is movable above the container along the vertical axis thereof; said head assembly having a cap receiving cavity with an upper abutment surface for matching the upper surface of the cap of containers of variable size and being provided with a plurality of movable sharpened means for catching the cap of the container when received in said cavity, there being provided first driving means for moving said sharpened means towards the cap of the container to catch it and second driving means for moving the sharpened means in at least one further direction to remove the cap from the container.

BRIEF DESCRIPTION OF THE DRAWINGS

The characteristics and advantages of the present invention will appear evident from the following detailed description of an embodiment thereof illustrated as non-limiting example in the enclosed drawings, in which.

DETAILED DESCRIPTION OF THE INVENTION

Figure 1:
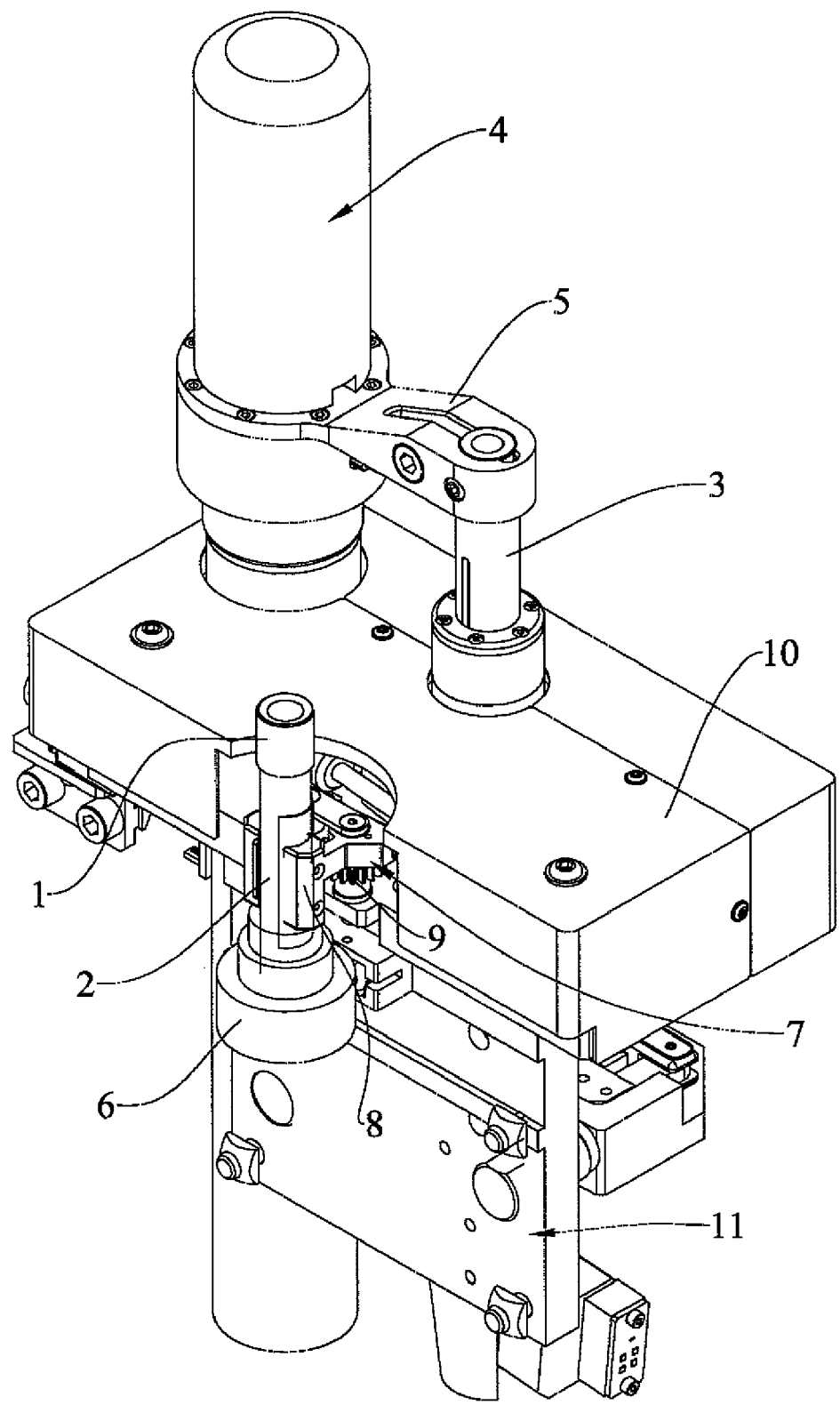
FIG. 1 is a perspective view of an apparatus according to the present invention in a rest position.
Figure 2:
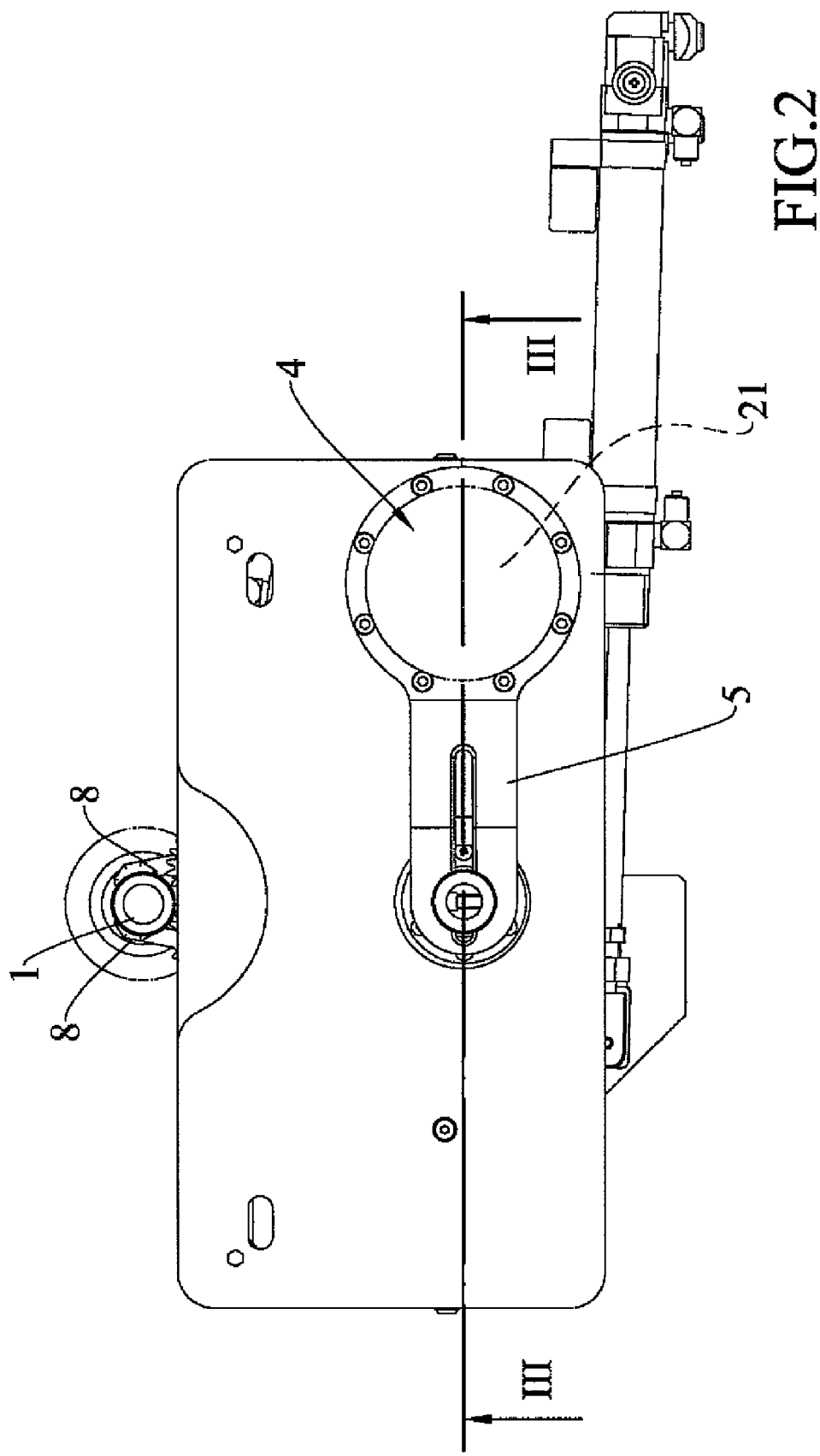
FIG. 2 is a top view of the apparatus of FIG. 1.
Figure 3:
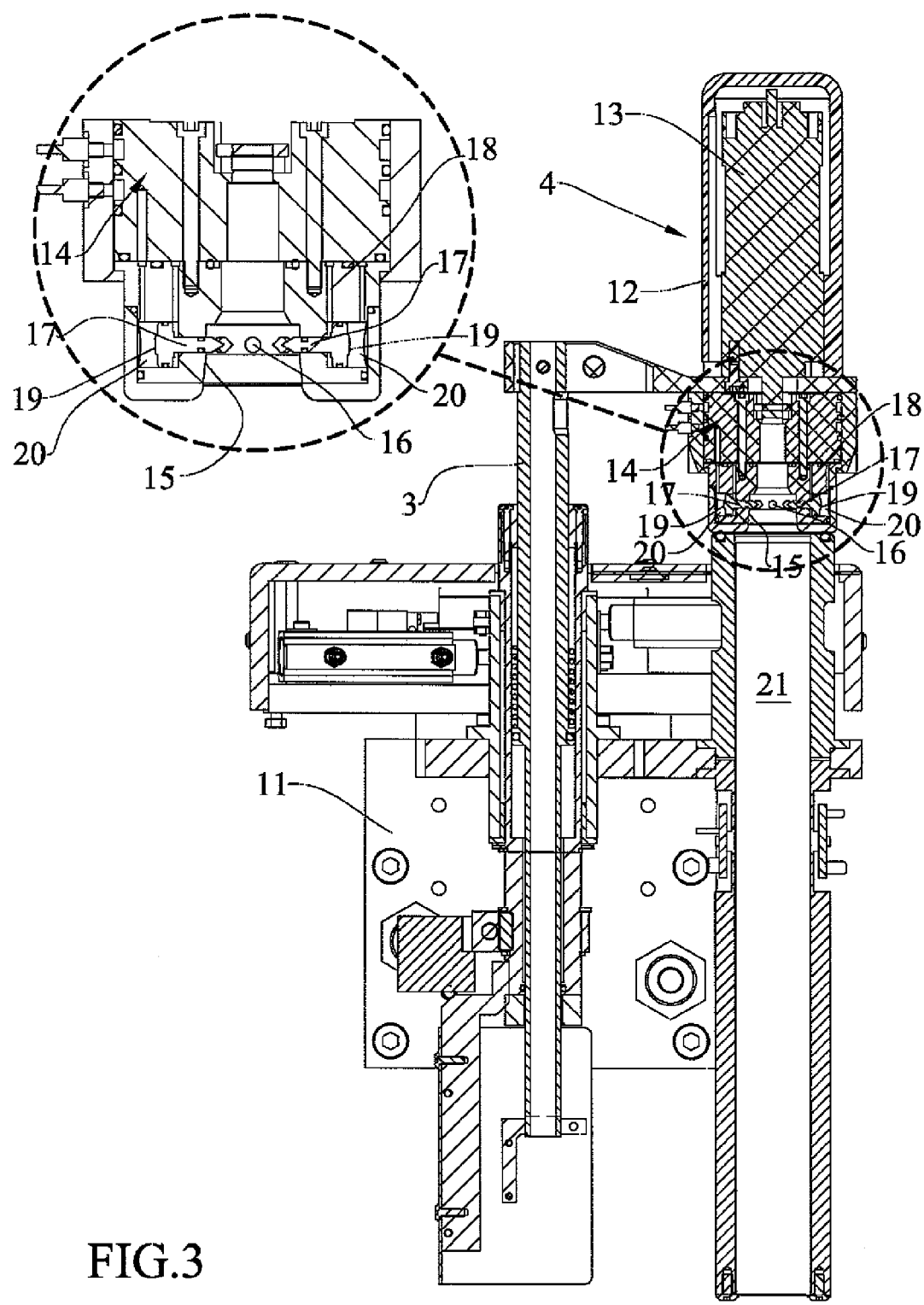
FIG. 3 is a sectional view according to line III-III of FIG. 2.

A decapper or apparatus for removing a screw cap 1 from a tubular specimen container 2 is shown in FIGS. 1-3 and comprises a rotatably and vertically movable shaft 3 upon which a head assembly 4 is mounted by means of a bracket 5. The shaft 3 is rotatably and slidingly supported by a fixed frame 11 and has fixed to its lower end an optical counter 60 cooperating with an optical ruler 61 (FIGS. 6-9) to form an optical encoder for detecting the vertical position of the shaft 3 enabling the head assembly 4 to self adapting to containers of variable height and being able to communicate said height to the decapper control unit.

The specimen container 2 is supported by a carrier 6 and is blocked by a grasping device 7 which is included in the housing 10 and comprises grasping arms 8 actuated by driving means 9 (FIGS. 1, 2, 16 and 17).

Figure 16:
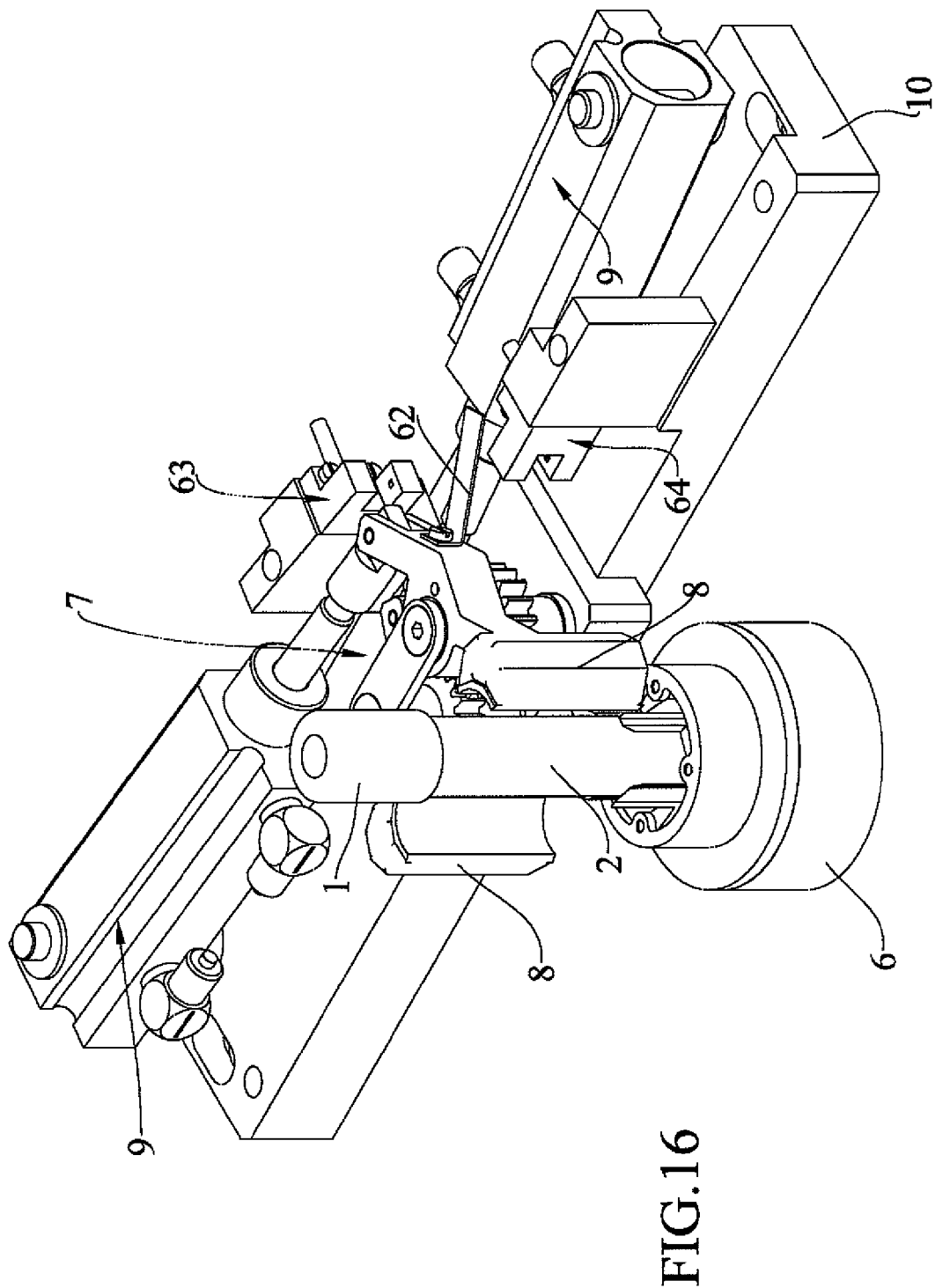
FIG. 16 is a perspective view of a part of the apparatus including grasping means for the container and a sensor for detecting the diameter of the container, the grasping means being shown in open position.
Figure 17:
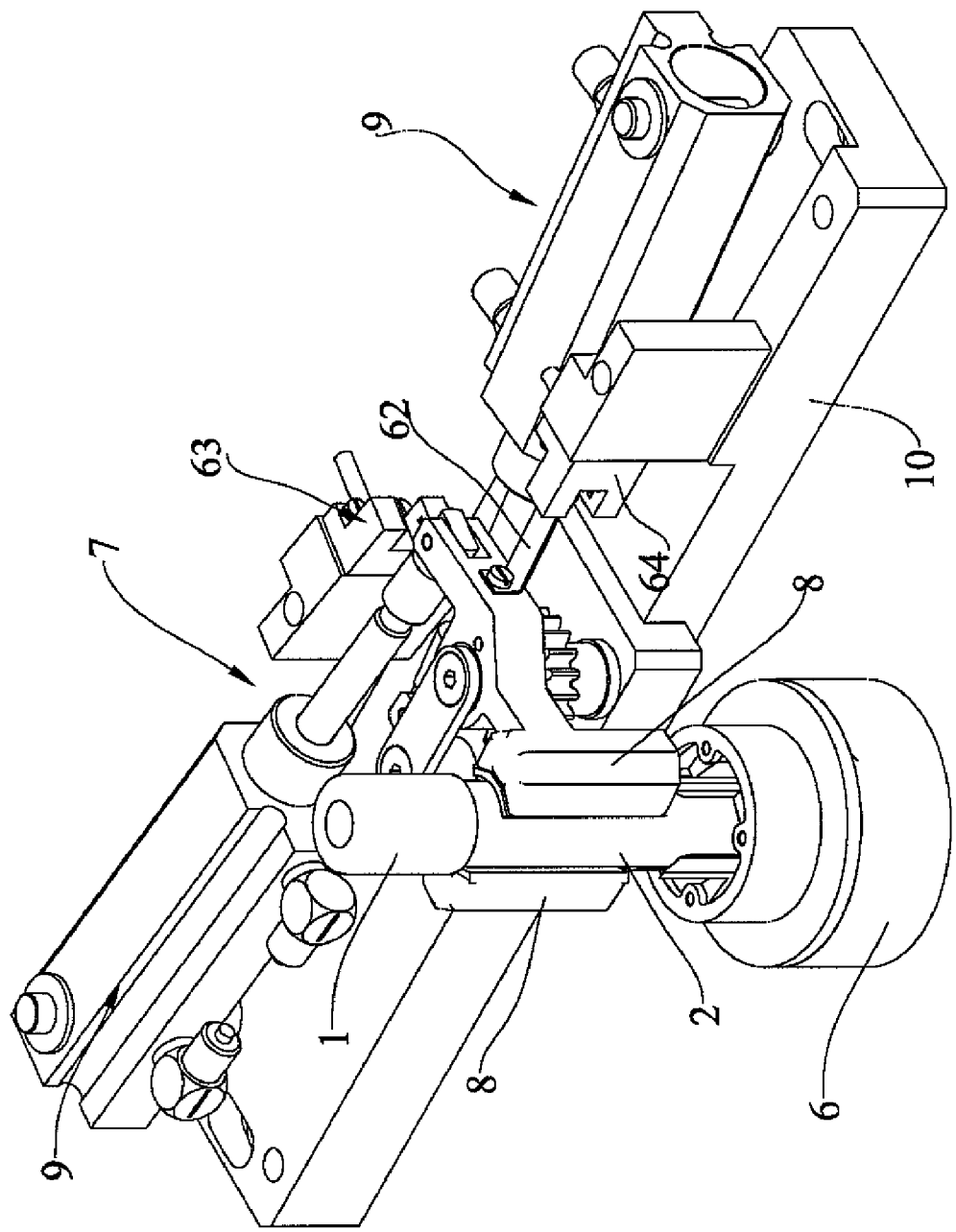
FIG. 17 is a perspective view similar to FIG. 16 with the grasping means in closed position.

A rod 62 is fixed to one of the arms 8 and cooperates with two optical readers 63 and 64 to detect the closed or open position of the grasping arms 8 (FIGS. 16 and 17).

The frame 11 connects the apparatus to a conveyor belt system (not shown) on which the carrier 6 is movable with its container 2.

Said head assembly 4 comprises a casing 12 in which a motor 13 for driving a rotor 14 is housed (FIG. 3).

The rotor 14 is provided with a cavity 15 having an upper abutment surface 65 (FIGS. 3, 7, 8,11 and 12) and peripheral radial holes 16 for guiding catching needles 17, with inward tips 30, which are radially movable, with respect to the vertical axis of the head assembly 4, by a pneumatic device 18 included in said head assembly 4.

Each needle 17 rotates with the rotor 14 and comprises a head member 19 included in a guiding chamber 20 of the rotor 14.

The apparatus comprises also a waste chute 21 for the removed cap 1.

Starting with the situation of FIG. 1, the specimen container 2 is firmly blocked by the grasping arms 8 to make sure that the container is not removed from its carrier 6. Blocking of the container is detected by the sensor 63, 64 (FIGS. 16, 17).

Figure 4:
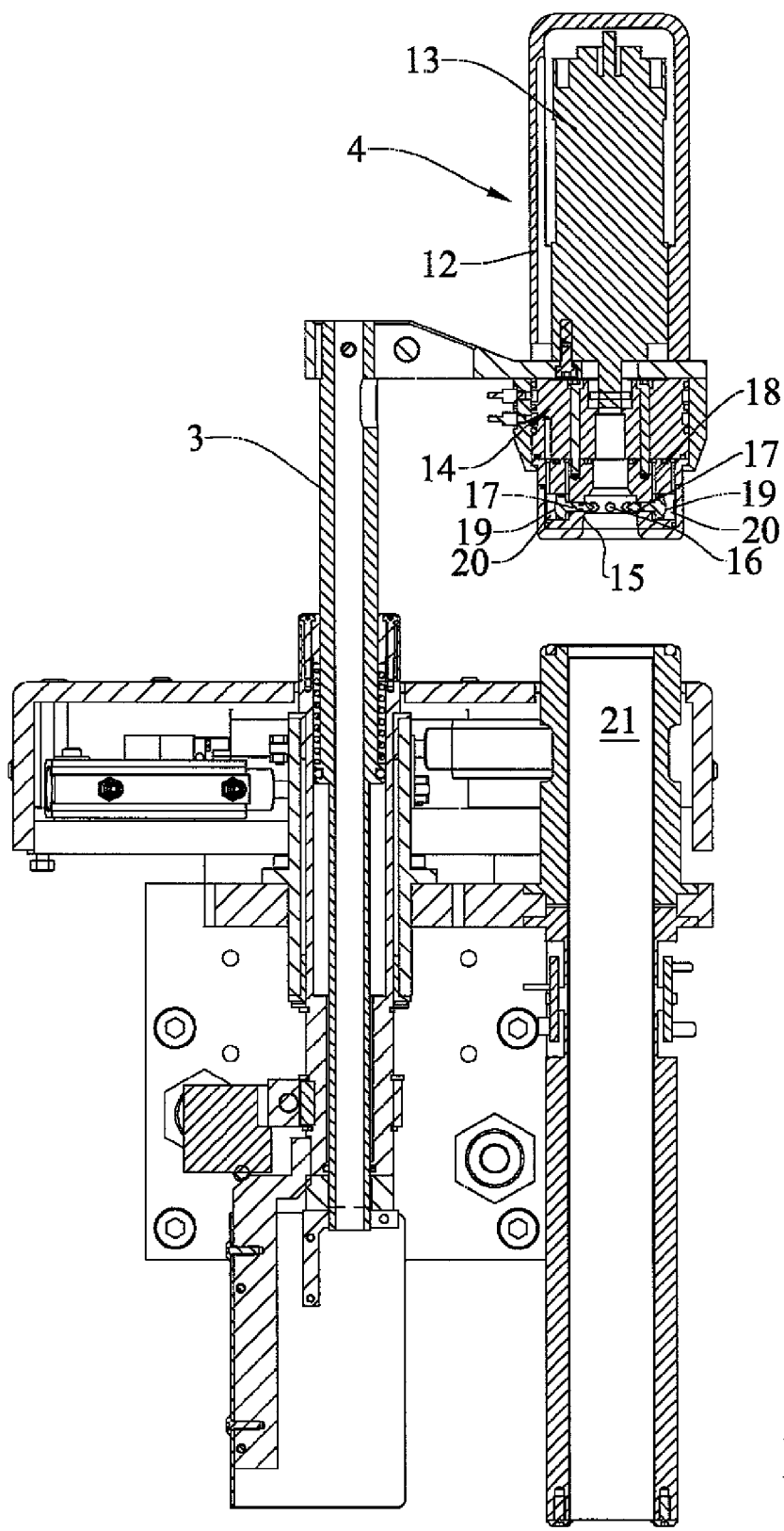
FIG. 4 is the same sectional view of FIG. 3 in a first working position.
Figure 5:
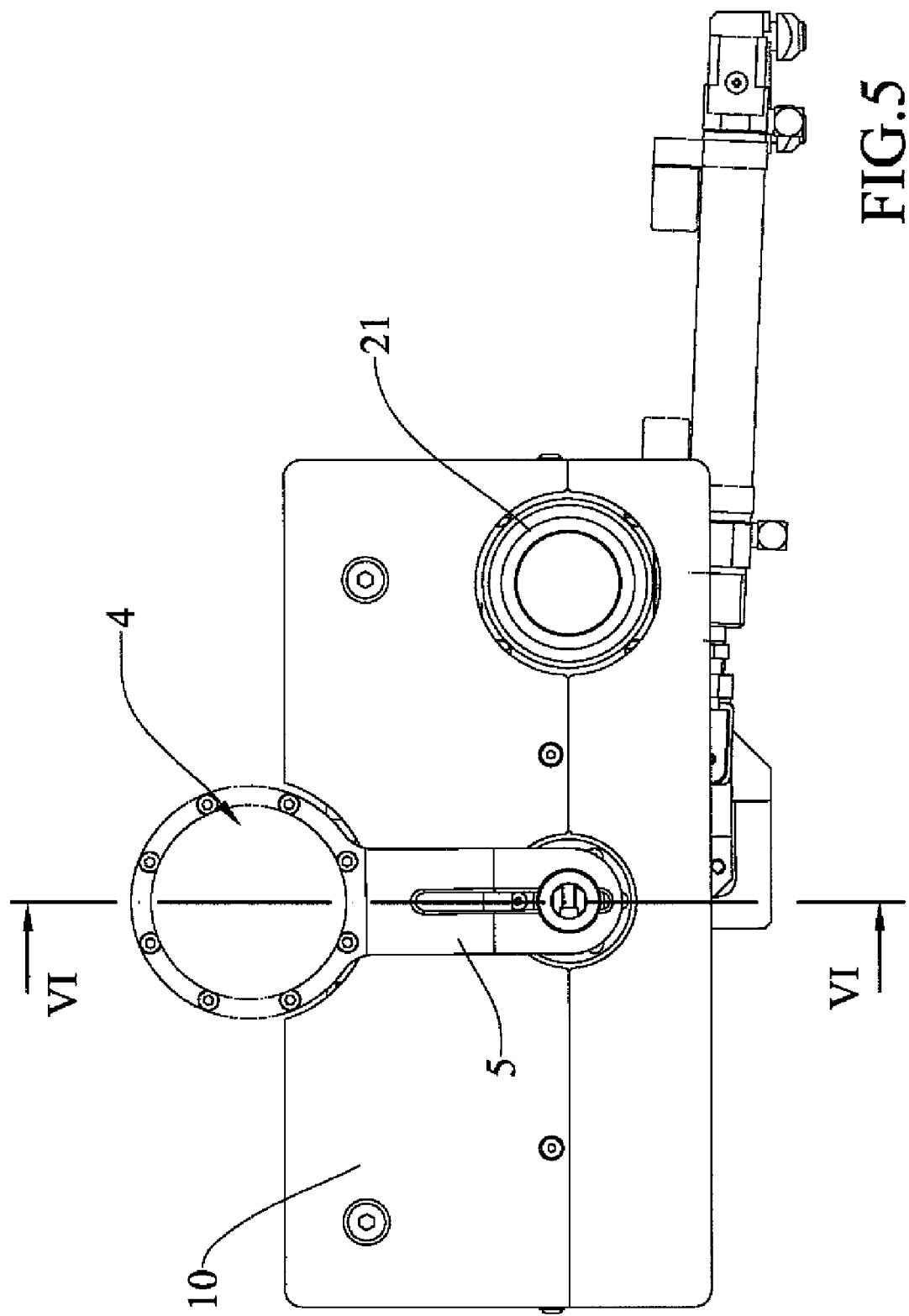
FIG. 5 is a top view of the apparatus in a second working position.
Figure 6:
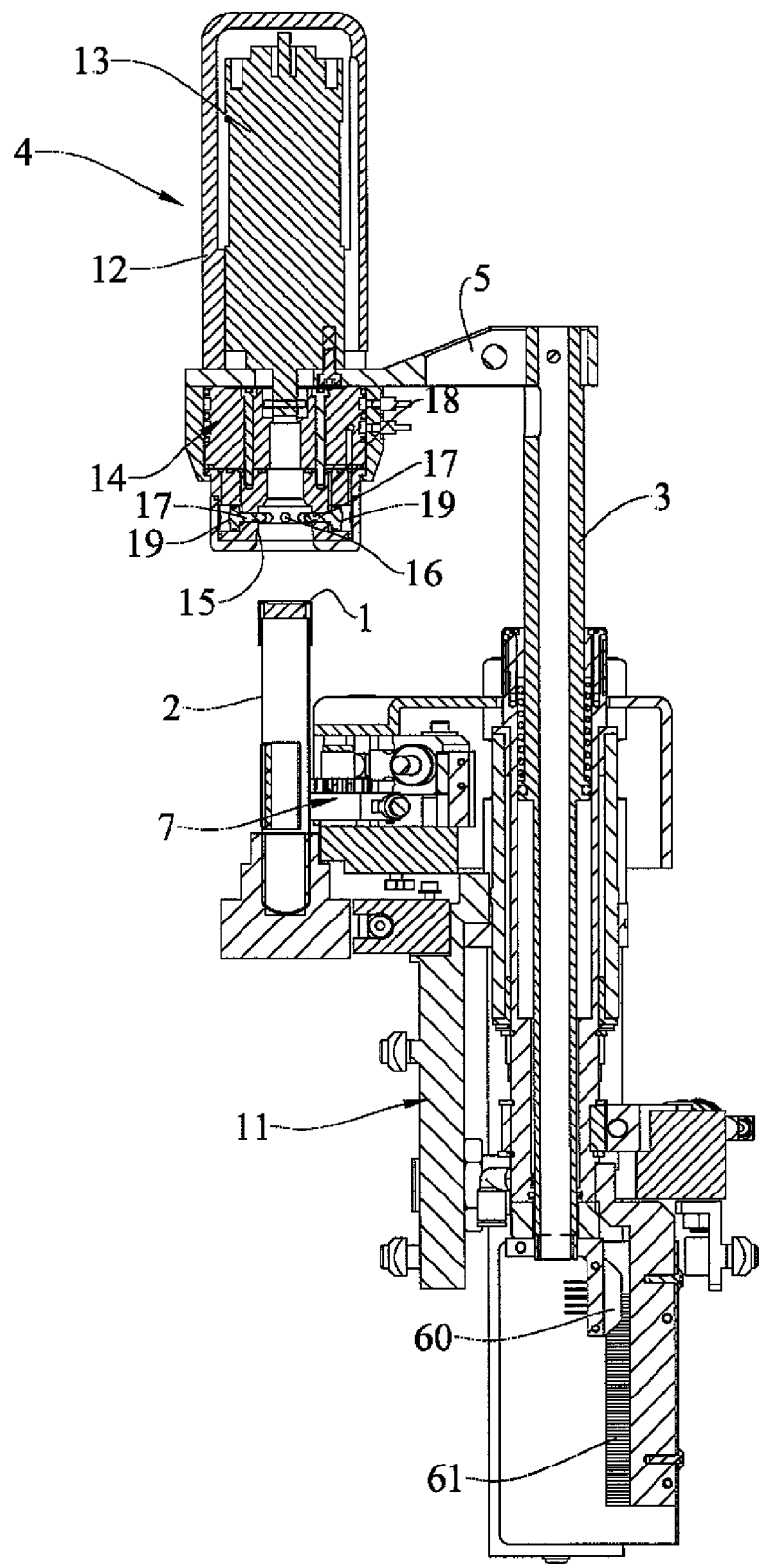
FIG. 6 is a sectional view according to line VI-VI of FIG. 5.

The mounting shaft 3 now upraises (FIG. 4) and rotates of about 90° until the head assembly 4 is over the cap 1 of the container 2 (FIGS. 5-6).

Then the mounting shaft 3 goes down until the cap 1 is coupled inside the cavity 15 (FIG. 7) in abutment with the upper surface 65 of the cavity. The optical encoder 61, 60 detects the vertical position of the shaft and provides a corresponding electric signal for the control unity of the automated laboratory system to which the decapper apparatus belongs. The abutment provided by the cavity surface 65 allows the cavity to receive containers of variable size.

The encoder 61, 60 detects the vertical stroke of the shaft 3, corresponding to the length of the container 2, and informs the control unit of the laboratory system.

Figure 7:
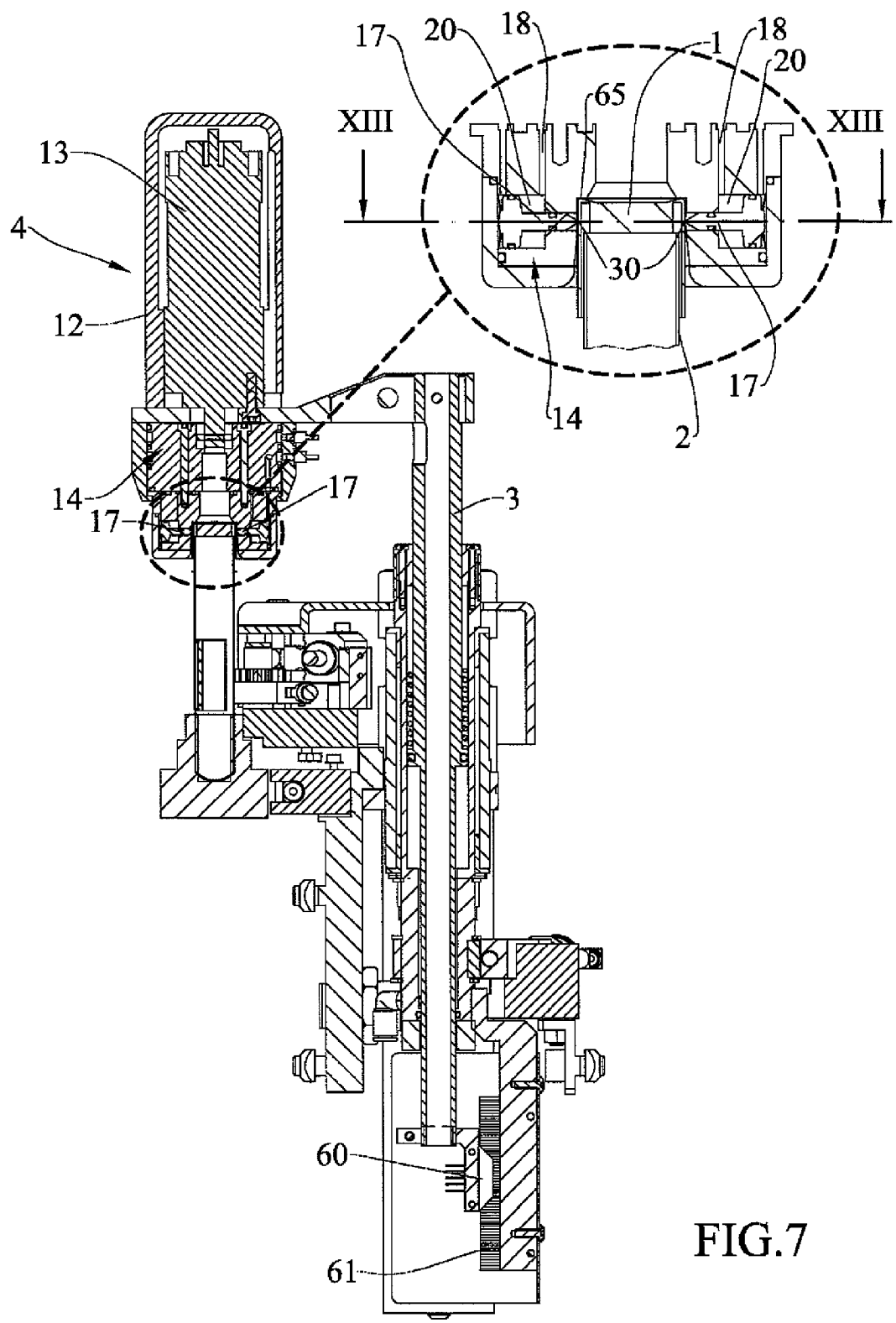
FIG. 7 is the same sectional view of FIG. 6 in a third working position.
Figure 13:
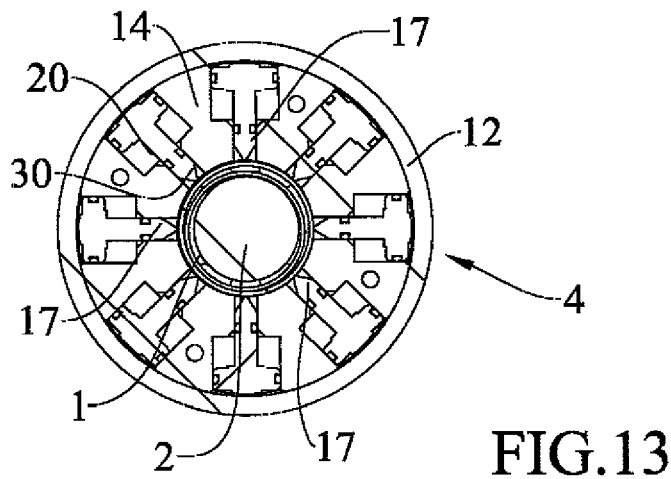
FIG. 13 is an sectional view according to line XIII-XIII of FIG. 7.

The catching needles 17 are still in a rest outward position (see enlarged window of FIG. 7 and FIG. 13).

Figure 8:
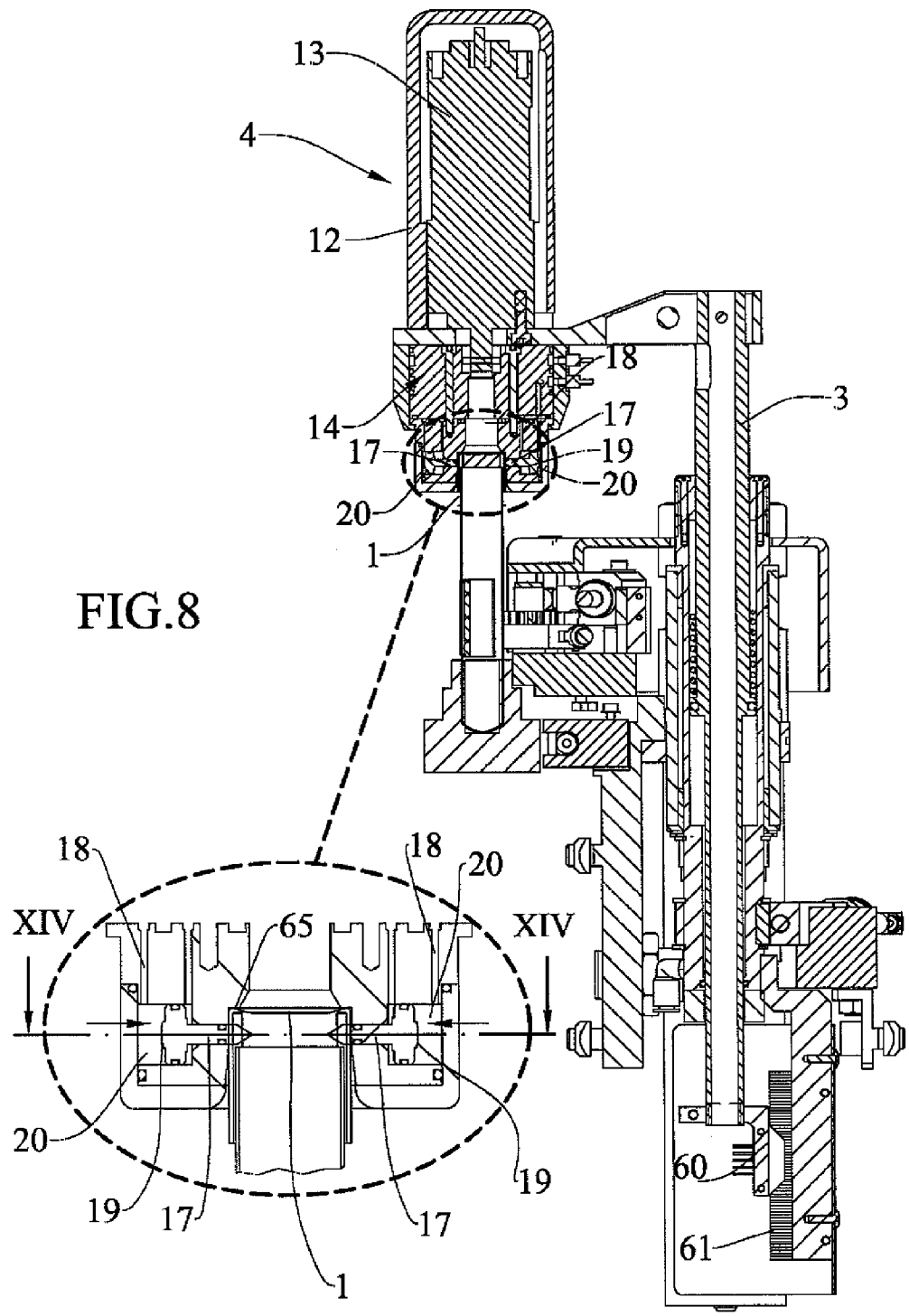
FIG. 8 is the same sectional view of FIG. 6 in a fourth working position.

A control unit commands the pneumatic device 18 to move inwardly the needles 17 which go through the holes 16 and catch the cap 1 (FIG. 8).

Figure 14:
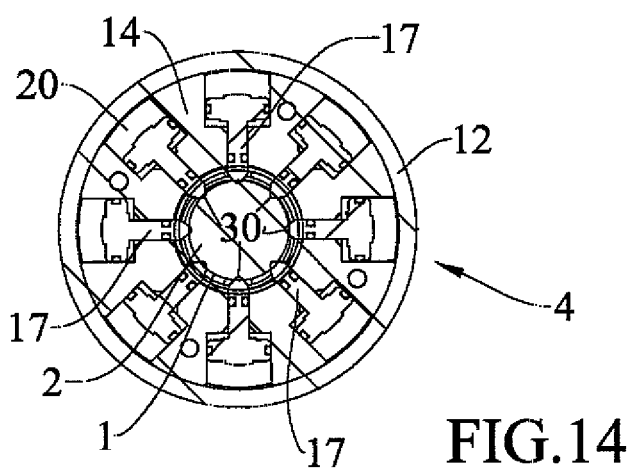
FIG. 14 is a sectional view according to line XIV-XIV of FIG. 8.

The pneumatic cavity 18 injects air into the external portion of the chamber 20 pushing inwardly the head members 19 of the needles 17 (see enlarged window of FIG. 8 and FIG. 14).

By said catching needles 17, the cap is firmly caught in a plurality of points where the cap is slightly deformed but not perforated.

These deformations allow a firm grip by the head assembly 4 on the cap 1 without damage for the threads of the cap 1 and of the head of the container 2.

Figure 15:
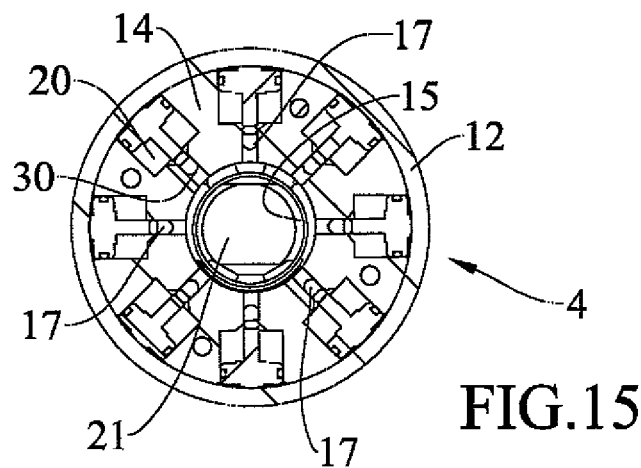
FIG. 15 is a sectional view according to line XV-XV of FIG. 12.

The catch force is perfectly balanced because the needles 17 have the same angular distance between each others and are pointed to the centre of a circle, defined by the casing 12, of which the needles 17 are the radiuses (FIGS. 13-15).

Said apparatus is provided with eight needles 17, but it is also possible to have a good catch with less needles 17, three for example.

Nevertheless it is better to provide a plurality of needles 17, particularly more than four needles 17, because the catch force is increased and better balanced.

Figure 9:
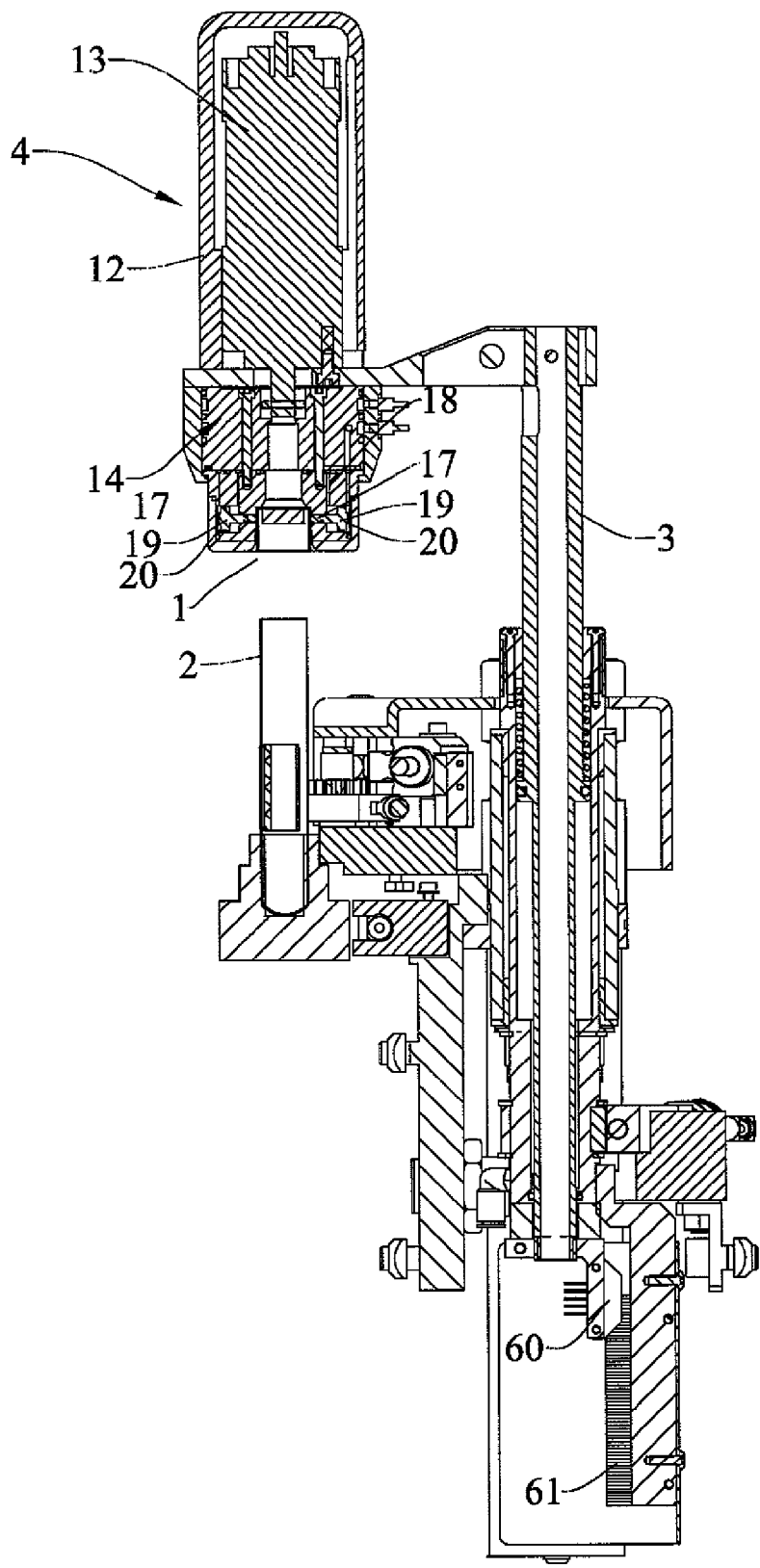
FIG. 9 is the same sectional view of FIG. 6 in a fifth working position.

For removing the cap 1 from the head of the container 2, the motor 13 drives the unscrewing rotation of the rotor 14, with the needles 17, and simultaneously the head assembly 4 upraises (FIG. 9).

Figure 10:
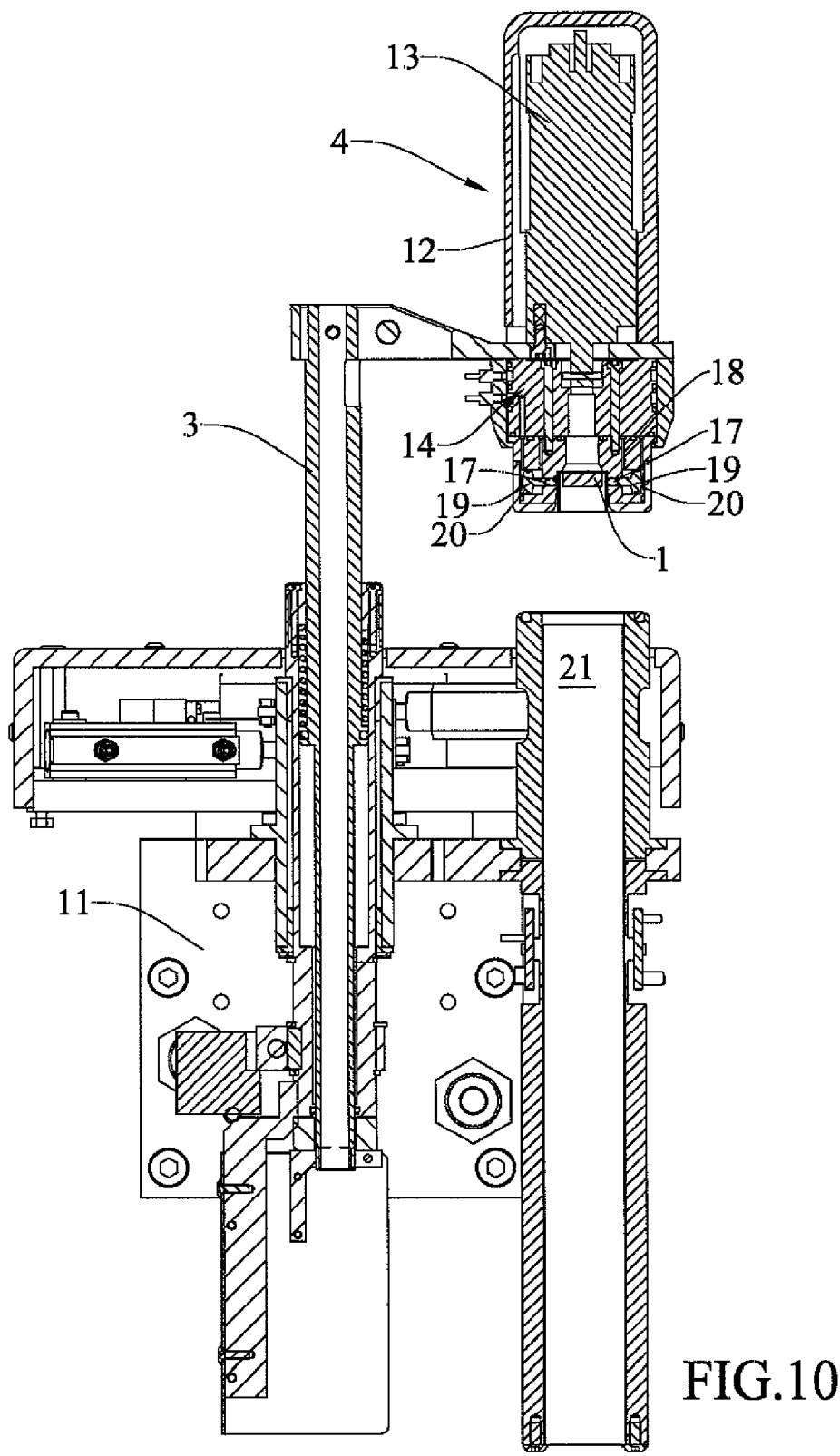
FIG. 10 is the same sectional view of FIG. 6 in a sixth working position.
Figure 11:
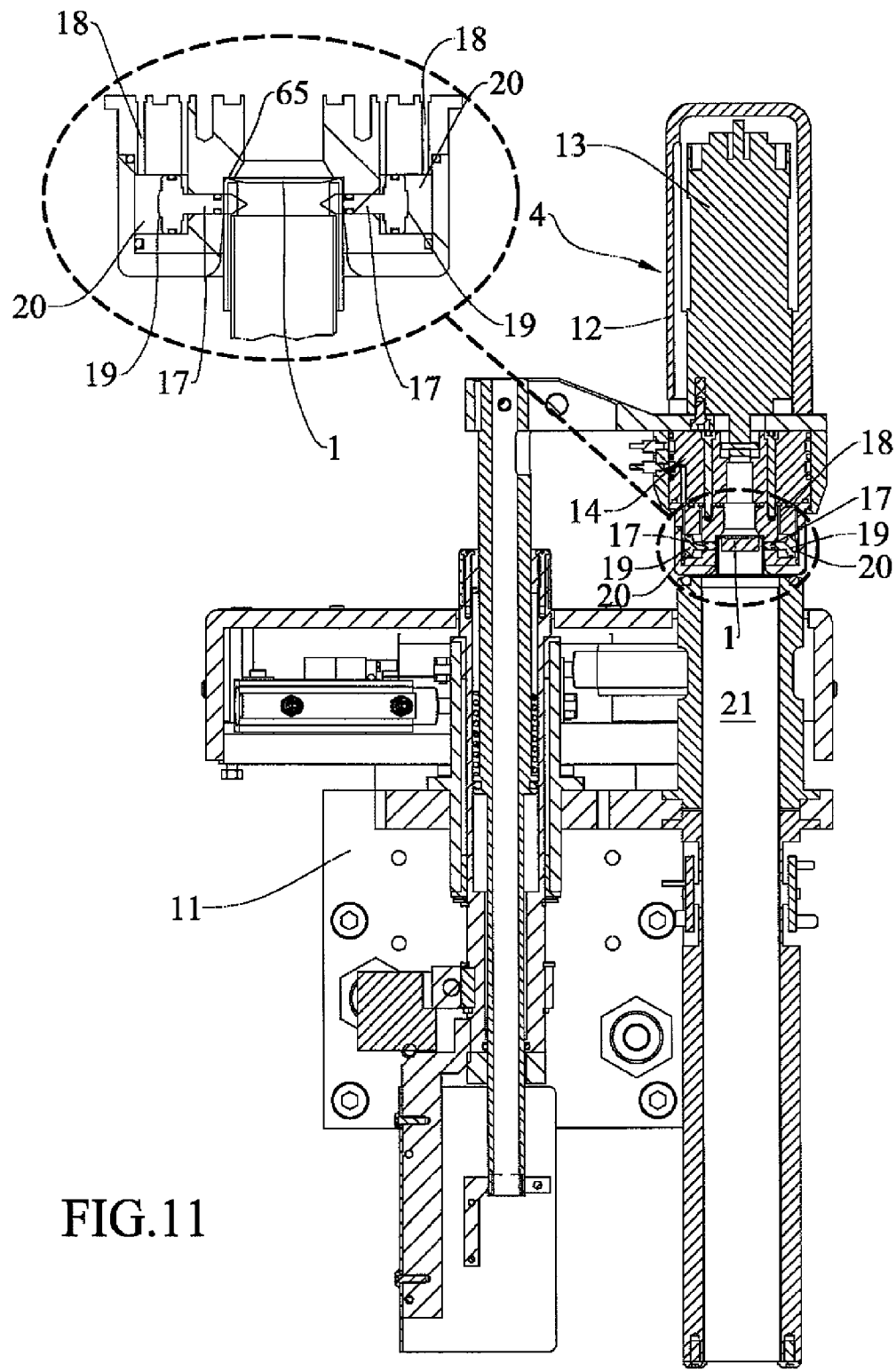
FIG. 11 is the same sectional view of FIG. 6 in a seventh working position.
Figure 12:
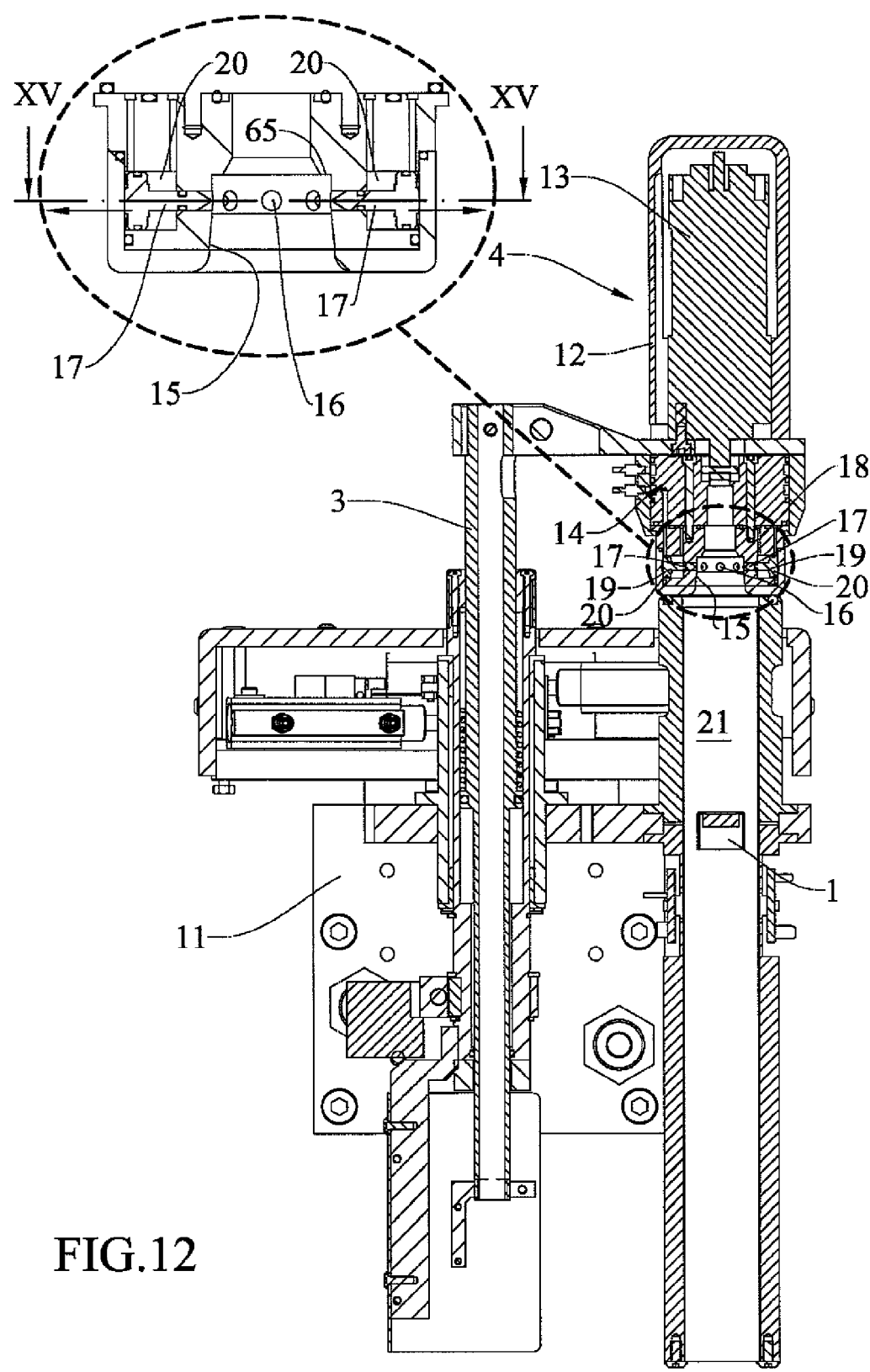
FIG. 12 is the same sectional view of FIG. 6 in a eighth working position.

Finally the shaft 3 has a 90° back rotation, for positioning the removed cap 1, over the waste chute 21 (FIG. 10). When the head assembly 4 is gone down above the opening of the waste chute 21, the pneumatic device 18 drives outward the needles 17, allowing the cap 1 to fall into the waste chute 21 (FIGS. 11-12, 15).

The apparatus comprises detecting (not shown) sensors on the head assembly 4 for detecting the catch of the cap 1, and in the waste chute 21 for detecting the release of the cap 1, that is the end of the decapping work.

This apparatus is also suitable for pressure caps. In this embodiment the steps for removing a pressure cap 1 are the same described above for a screw cap 1.

The invention claimed is:

1. An apparatus for removing caps from tubular specimen container supported on a carrier and blocked by a grasping device including grasping arms actuated by driving means, comprising a head assembly which is movable above a container of variable height along the vertical axis thereof in coordination with an optical counter and a control unit, said head assembly having a cap receiving cavity with an upper abutment surface for matching the upper surface of the cap of containers of variable size, wherein said head assembly is provided with a rotor and a motor for driving the rotor, the rotor having radial passing holes for radially guiding sharpened members between a rest position and a catch position of the cap of the container, the rotor driving the rotation of the sharpened members catching the cap with respect to the container fixed in a vertical position by the grasping arms of a fixed frame, and a waste chute for a removed cap.

2. The apparatus according to claim 1, wherein said sharpened members cause a slight deformation of the cap in peripheral points where the sharpened members engage said cap.

3. The apparatus according to claim 2, further comprising a pneumatic device radially driving the sharpened members.

4. The apparatus according to claim 1, further comprising a pneumatic device radially driving the sharpened members.

5. The apparatus according to claim 1, wherein said sharpened members comprise catching needles.

6. The apparatus according to claim 5, wherein said catching needles comprise head members housed in chambers arranged inside the rotor.

7. The apparatus according to claim 5, further comprising three or more catching needles arranged with the same angular distance between each other, with their tips towards a center of a virtual circle, being said center on the axis of the container.

8. The apparatus according to claim 1, wherein two sensors are associated to said grasping arms to detect the closed and open positions thereof.

9. The apparatus according to claim 1, wherein a sensor is provided to detect the length of the vertical movement of the head assembly.

10. The apparatus according to claim 1, wherein the head assembly is mounted on a rotatably and vertically movable shaft which is self adapting to any height of the container and is capable, by using ruler sensors, to detect and communicate the height of said container to the control unit.

\* \* \* \* \*